(12) United States Patent
Chae et al.

(10) Patent No.: US 9,023,597 B2
(45) Date of Patent: *May 5, 2015

(54) ONE STEP DIAGNOSIS BY DENDRON-MEDIATED DNA CHIP

(75) Inventors: Chi-Bom Chae, Seoul (KR); Soon Jin Oh, Seoul (KR)

(73) Assignee: Korea Materials & Analysis Corp., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/616,761

(22) Filed: Dec. 27, 2006

(65) Prior Publication Data

US 2008/0008990 A1    Jan. 10, 2008

Related U.S. Application Data

(60) Provisional application No. 60/755,503, filed on Dec. 29, 2005.

(51) Int. Cl.
    *C12Q 1/68*    (2006.01)

(52) U.S. Cl.
    CPC ............ *C12Q 1/6834* (2013.01); *C12Q 1/6837* (2013.01)

(58) Field of Classification Search
    None
    See application file for complete search history.

(56) References Cited

U.S. PATENT DOCUMENTS

| 5,750,347 | A  | * | 5/1998 | Bagasra et al. ................... 435/6 |
| 5,919,626 | A  | * | 7/1999 | Shi et al. ........................... 435/6 |
| 6,280,930 | B1 | * | 8/2001 | Backus et al. ................ 435/6.18 |
| 2003/0039957 | A1 | * | 2/2003 | McCarthy et al. ................ 435/5 |
| 2004/0023248 | A1 | * | 2/2004 | O'Malley .......................... 435/6 |
| 2004/0029258 | A1 | * | 2/2004 | Heaney et al. ............. 435/287.2 |
| 2005/0037413 | A1 |   | 2/2005 | Park |
| 2007/0190537 | A1 | * | 8/2007 | Park et al. ......................... 435/6 |
| 2008/0064070 | A1 | * | 3/2008 | Park et al. .................... 435/91.2 |

FOREIGN PATENT DOCUMENTS

| KR | 2004-0002383 |   | 9/2004 |            |
| WO | WO 96/31622 A1 |   | 10/1996 |            |
| WO | WO 01/48242 A2 |   | 7/2001 |            |
| WO | WO 02/20469 A1 | * | 3/2002 | ............ C07C 271/12 |
| WO | WO 2004/020667 A1 |   | 3/2004 |            |
| WO | WO 2004/079002 A1 |   | 9/2004 |            |
| WO | WO 2005/075680 A1 |   | 8/2005 |            |
| WO | WO 2006/000647 A1 |   | 1/2006 |            |
| WO | WO 2007/119066 |   | 10/2007 |            |

OTHER PUBLICATIONS

Hong et al, Self-Assembly of a Dendron through Multiple Ionic Interaction to Give Mesospacing between Reactive Amine, Langmuir 2003, 19, 2357-2365.*
2008, FASTSTART high Fidelity PCR System for the Diagnostic Industry, published by Roche Diagnostics, Manheim, Germany, pp. 1-2.*
Benters et al., DNA microarrays with PAMAM dendritic linker systems, Nucleic Acids Research, 2002, Vo. 30, No. 2, e10, pp. 1-7.*
Huber et al., Accessing Single Nucleotide Polymorphisms in Genomic DNA by Direct Multiplex Polymerase Chain Reaction Amplification on Oligonucleotide Microarrays, Analytical Biochemistry 303, 25-33 (2002).*
Bell et al., Technical Notes Synthesis and Characterization of Covalently Linked Single-Stranded DNA Oligonucleotide-Dendron Conjugates, Bioconjugate Chem. 2003, 14, 488-493.*
Auroux et al., Miniaturised nucleic acid analysis, Miniaturisation for Chemistry , Biology & Bioengineering, Lab Chip, 4, pp. 534-546, First published as an Advance Article on the web Oct. 22, 2004.*
Oh et al., DNA microarrays on a dendron-modified surface improve significantly the detection of single nucleotide variations in the p53 gene, Nucleic Acids Research, 2005, vol. 33, No. 10 e90, pp. 1-8, published online Jun. 6, 2005.*
Guo et al. (Direct fluorescence analysis of genetic polymorphisms by hybridization with oligonucleotide arrays on glass supports, Nucleic Acids Research, 1994, vol. 22, No. 24, pp. 5456-5465).*
Gravitt et al. (Genotyping of 27 Human Papillomavirus Types by Using L1 Consensus PCR Products by a Single-Hybridization, Reverse Line Blot Detection Method, Journal of Clinical Microbiology, Oct. 1998, p. 3020-3027).*
Gerberding (Report to Congress: Prevention of Genital Human Papillomavirus Infection, Centers for Disease Control and Prevention Department of Health and Human Services, Jan. 2004).*
Hong, BJ, et al. "Nanoscale-controlled spacing provides DNA microarrays with the SNP discrimination efficiency in solution phase", Langmuir, (2005); 21(10): 4257, (abstract only).
Trau, D, et al. "Genotyping on a Complementary Metal Oxide Semiconductor Silicon Polymerase Chain Reaction Chip with Integrated DNA Microarray", Anal. Chem.(2002) 74, 3168-317.
Oh, SJ, et al. "DNA microarrays on a Dendron-modified surface improve significantly the detection of single nucleotide variations in the p53 gene", Nucleic Acids Research (2005).
Hong, BJ, et al. "DNA microarrays on nanoscale-controlled surface", Nucleic Acids Research (2005), vol. 33, No. 12 e106 doi: 10:1093/mar gni109.

* cited by examiner

*Primary Examiner* — Christopher M Babic
*Assistant Examiner* — Aaron Priest
(74) *Attorney, Agent, or Firm* — Sughrue Mion, PLLC

(57) ABSTRACT

This invention relates to chips containing nucleic acid probes or primers and their use in methods to detect nucleic acid molecules. The invention includes DNA chips in contact with a thermocycler capable of automatically regulating the temperature, temperature cycle times, and number of temperature cycles of the chips to provide genetic diagnosis in one step.

19 Claims, 9 Drawing Sheets

1896 G

1896 A

1896 G

1896 A

ONE STEP DIAGNOSIS BY DENDRON-MEDIATED DNA CHIP

RELATED APPLICATIONS

This application claims benefit of priority from U.S. Provisional Patent Application 60/755,503, filed Dec. 29, 2005, which is hereby incorporated by reference as if fully set forth.

FIELD OF THE INVENTION

This invention relates to chips containing nucleic acid probes or primers and their use in methods to detect nucleic acid molecules. The invention also provides DNA chips and their use in the diagnosis of genes in one step.

BACKGROUND OF THE INVENTION

Generally speaking, DNA or gene chips have being developed for detection of infectious pathogens, disease-causing genes, mutations, and expression levels of genes, etc. In some instances, the technology has also been adapted for diagnosis at hospitals and clinics. In other instances, various technologies have been consolidated and optimized for convenient use and for reliable decisions in connection with clinical diagnosis.

For detection of certain DNA sequence(s) in a biological sample with use of a DNA chip, the following steps are typically followed:
(1) secure tissues, cells and/or biological fluids,
(2) extraction of DNA or RNA,
(3) amplification of certain sequences or nucleic acid regions of interest, typically by polymerase chain reaction (PCR), with use of appropriate primers in the presence of deoxynucleotide triphosphates, one of which is labeled with fluorescent compound,
(4) purification of the amplified DNA,
(5) add the purified amplified DNA to a solid surface, such as a glass slide, containing attached short single stranded DNAs that act as capture probes by being complementary to the amplified DNA,
(6) hybridization of the fluorescently labeled amplified DNA to a capture probe to form double stranded DNA attached to the solid surface,
(7) scanning the fluorescence of the double-stranded DNA formed on the surface of the chip, and
(8) analysis of the data.

These processes are long, and cumbersome, and loss of samples occur during purification of reaction products. The losses cause variation of the final results.

The Polymerase Chain Reaction (PCR) is used widely for amplification of a minute amount of a defined DNA sequence to be an amount sufficient for analysis such as DNA sequencing, detection by gel electrophoresis, and for DNA chip-based analysis. Generally, the PCR process involves denaturation of DNA (strand separation) at a high temperature, annealing of primers that are complementary to either ends of a DNA region to be amplified, and chain elongation from the annealed primers in the presence of thermostable DNA polymerase and the four deoxynucleotide triphosphates. These processes require specific temperatures: for example, 90° C. or above for denaturation, 55-65° C. for annealing, and 72° C. for chain elongation. Denaturation, annealing and chain elongation are repeated continuously until desired amount of DNA is amplified, typically 20-30 cycles. Therefore, PCR requires a programmable thermocycler.

A DNA chip is typically a slide on which capture probes (short single-stranded DNA) are immobilized in a high density format. They are used for analysis of the presence of certain DNA or RNA sequences, the presence of mutation(s), and expression (transcription) of certain genes in cells or tissues.

Usually, a glass slide is coated with chemicals to attach DNA to the glass. The chemicals should not only attach the DNA to the glass surface but also minimize non-specific binding and noise. For example, the chemicals contain silanated, silylated, or poly-L-lysine as a source of amine or aldehyde group for attachment of DNA. Recently, dendrons have been developed for use in biochip. When a chip is coated with dendrons, one can control spacing between capture probes and this also allows reduction of steric hinderance and concomitant increase in sensitivity. Korean patent 10-0383080-0000 and published U.S. Patent Application 2005/0037413 describe dendrons provide controlled spacing as well as density of amines on dendron.

When DNA chip slides are used, the sequence of steps is to amplify the DNA (labeling the DNA with fluorescent group at the same time) and then purify the DNA. The amplified DNA is denatured by heating and added to the surface of capture probes for annealing. After hybridization, the slide is washed and the fluorescent double-stranded DNA is detected by scanning and the data are analyzed.

As described above, the use of DNA chip requires extraction of DNA or RNA from cells, gene amplification and purification, and DNA hybridization. This requires different instruments for gene amplification and hybridization, and considerable time is required for gene amplification and purification (as much as one day). Also, the cost of chemicals and disposable items is high. There is also loss of sample during purification of gene amplification products. Therefore, there is need for streamlining the cumbersome processes involved in use of gene chips.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

BRIEF SUMMARY OF THE INVENTION

This invention relates to methods for gene diagnosis by DNA chip in one step. Put differently, the methods may be considered as integrating all steps needed for use of a DNA chip to detect nucleic acid molecules. The invention may be advantageously used to conduct DNA or RNA based diagnosis, via nucleic acid detection, in one chamber on a slide in an automatic or semi-automatic manner by simply changing the temperature and duration of a series of reactions using a temperature cycler.

Thus, and in a first aspect, the invention includes a DNA chip with a plurality of nucleic acid probes immobilized on a surface of the chip. The surface may be one facing an enclosed, interior space (or volume) on the chip. The enclosed volume may be a chamber with a removably attached side or other opening (which may be closed) capable of containing a liquid reaction volume for preparing or manipulating nucleic acid molecules. In operation, the reaction volume contains a nucleic acid molecule to be detected, which molecule is amplified at least in part. The substance containing a nucleic acid molecule to be detected may be added directly to the reaction volume so that matter normally or commonly found with the nucleic acid molecule is also present in the reaction volume. So in some cases, a biological sample containing the nucleic acid to be detected is added to the reaction volume. The sample may contain a cell with the nucleic acid molecule to be detected. The reaction volume would also contain other reagents necessary for nucleic acid amplification.

The amplification may be repetitive, such that multiple cycles of nucleic acid amplification occur to produce a detectable amount of amplified nucleic acid material. The amplified nucleic acid material is detected based upon its attachment to the chip via the immobilized probes. The attachment is via base pair interactions between the material and the immobilized probes. In some embodiments, the interactions are facilitated by hybridization of the amplified material to the immobilized probes. After attachment of the amplified material, it is detected by a suitable means of scanning the chip and analyzing the presence or amount of attached amplified material.

In another aspect, the invention includes alternative methods of using a DNA chip as described herein wherein the nucleic acid probes immobilized on the chip surface is used as a primer in the amplification of the nucleic acid molecule to be detected. A second primer may also be used to amplify the nucleic acid molecule. The probe as primer is used to hybridize with the nucleic acid molecule to be detected followed by extension of the probe sequence (via a suitable nucleic acid polymerase) to produce a first nucleic acid strand complementary to the nucleic acid molecule being amplified. The optional second primer may then be used to synthesize the complementary second nucleic acid strand. The resultant amplified sequence is covalently attached to the probes, and so immobilized to the chip through the probes. The immobilized amplified sequences may then be detected by scanning the chip and analyzing the presence of the amplified sequences.

In many embodiments of the invention, detection of the amplified nucleic acids is aided by the use of one or more deoxynucleotide triphosphates attached to a detectable label. The triphosphates are incorporated into the amplified nucleic acid material by the polymerase used so that the amplified material contains the detectable label. The amplification of nucleic acid material, and so incorporation of the triphosphates, may be advantageously performed by use of the Polymerase Chain Reaction (PCR). This also allows the methods of the invention to be practiced by use of a programmable thermocycler which cycles the reaction volume on the chip.

The incorporation of a detectable label facilitates detection of the amplified nucleic acid material when they are attached to the chip. To further facilitate detection, the chip may be washed or rinsed to remove or reduce the amount of non-attached material so that interference with the detection of the amplified material is reduced or minimized.

As one non-limiting embodiment, a method of the invention for gene amplification and hybridization includes the following: (1) a slide; (2) the surface of the slide coated with dendron; (3) DNA capture probes attached on top of the dendron; (4) an incubation chamber created on the surface that contains the DNA capture probes; (5) direct addition of biological sample to a gene amplification reaction mixture in the chamber; (6) gene amplification and hybridization in the same incubation chamber on the slide; (7) scanning of the slide and analysis of the results.

In other embodiments, the methods of the invention may be adapted for performance in a semi-automated or fully automated manner.

The methods of the invention save time and effort, and minimize errors that arise from other methods using many handling steps, such as those involved in the isolation of amplified DNA material, gene amplification and purification, transfer of amplified samples to hybridization mixture, and so forth.

The details of additional embodiments of the invention are set forth in the accompanying drawings and the description below. Other features and advantages of the invention will be apparent from the drawings and detailed description, and from the claims.

DEFINITIONS

As used herein, the terms annealing and hybridization mean the same process: duplex formation between two strands of single stranded DNA by base complementarity or duplex formation between a DNA strand and a RNA strand by base complementarity.

The term "detect" or variants thereof includes both quantitative and qualitative methods of detection.

As used herein, "comprise" or "comprising" or "include" or "including" or variants thereof are used in the "open" sense such that the terms are inclusive and permit the presence of additional elements. The terms specify the presence of the stated features, steps, or components as recited without precluding the presence or addition of one or more features, steps, or components.

DESCRIPTION OF MODES OF PRACTICING THE INVENTION

General

Figure 1:
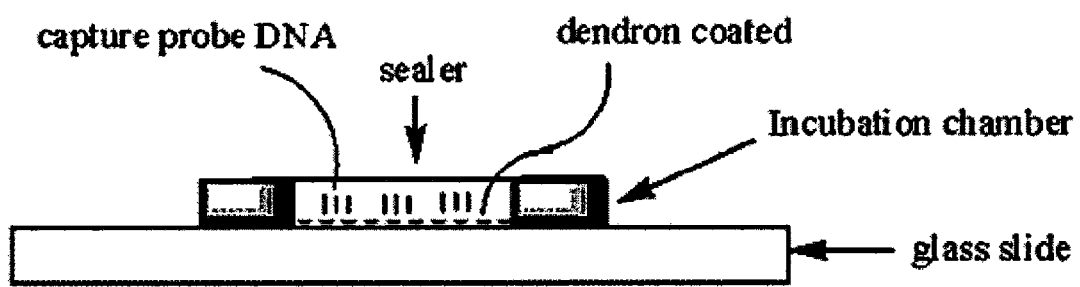
FIG. 1 illustrates, by a side cross-sectional view, a chip of the invention with an incubation, or reaction chamber.
Figure 2:
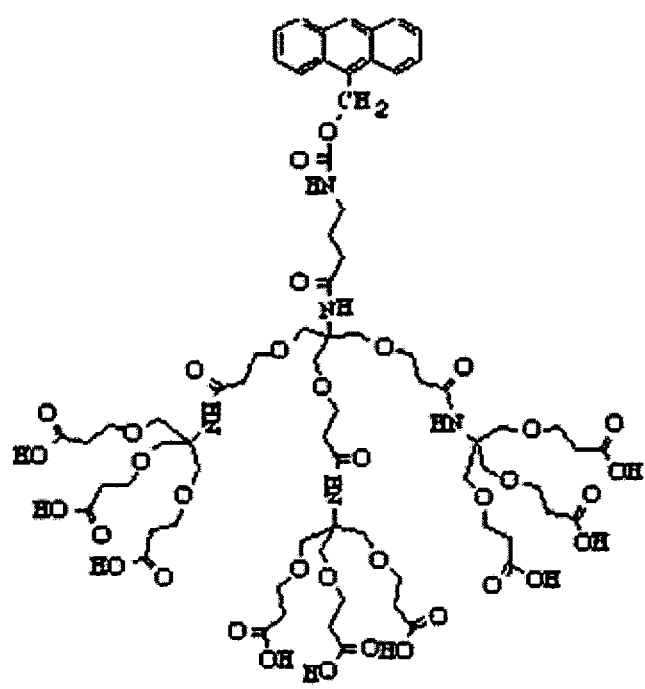
FIG. 2 shows a representative dendron that may be used in the practice of the invention.

The invention includes methods to simplify the amplification and detection of nucleic acid molecules. In some embodiments, the methods may be advantageously used in a "one step" process of detecting nucleic acid molecules in a biological sample with reduced handling and/or manipulation of the sample as well as the reactions used to amplify the nucleic acids.

A nucleic acid molecule to be amplified and detected according to the disclosed invention may be any that is of interest, such as genomic DNA of a cell, viral DNA or RNA of a (DNA or RNA) virus, or an RNA molecule. Thus a nucleic acid molecule may be a gene, a part of a gene or genome (such as all or part of a coding region), or an mRNA or part thereof as non-limiting examples.

In some embodiments, the nucleic acid molecule is present in whole blood, one or more cells, or a virus or viral particle. The nucleic acid molecule may be amplified, such as by PCR as described herein, or used for synthesis of a cDNA molecule. The nucleic acid molecule, or the amplified or cDNA form thereof, may also be hybridized to a probe containing solid surface as described herein. In some cases, the nucleic acid molecule is an RNA molecule of a virus which is present in an infected cell or viral particle and detected as described herein. The detection may be used to diagnose an infection by the virus (or presence of an infected cell) and/or presence of the virus.

The disclosed methods also make automation of gene diagnosis in hospitals and clinics possible. The disclosed methods save time and effort involved in nucleic acid (DNA or RNA) extraction from the cells and in purification of gene amplification products. The disclosed methods also minimize the loss of sample that occurs during the purification of gene amplification product thus increasing reproducibility and reliability of the diagnosis involving DNA chip.

Direct PCR and Detection

In one aspect, the invention includes methods for the direct PCR of a biological sample. In some embodiments, the sample is a cell or tissue containing sample wherein a nucleic acid molecule to be detected is present in the cell or tissue. The sample may be added directly to a reaction (or incubation) chamber on a solid surface, such as on a slide or chip, of the invention and mixed with the reagents needed for amplifying the nucleic acid molecule to be detected. Non-limiting examples include embodiments wherein the solid surface is on a microarray or in a cell or chamber of a solid medium. After amplification, the amplified material is hybridized to probes immobilized on the solid surface, such as on a chip surface within a chamber, and detected. The detection may be qualitative in nature with respect to the presence or absence of a nucleic acid molecule in a sample. Alternatively, the detection may be quantitative in nature to determine the amount of a nucleic acid molecule in a sample.

In some embodiments, a method for detecting a nucleic acid molecule in a sample is provided. The method comprises amplification of the nucleic acid molecule in the presence of a single stranded nucleic acid probe complementary to the molecule where the probe is attached to a solid surface by a dendron. If the nucleic acid molecule is double-stranded, the probe is complementary to one strand of the molecule. The method may be used to amplify a nucleic acid molecule, in a sample, by use of two primers in a polymerase chain reaction (PCR) to produced amplified nucleic acid material; followed by allowing said amplified nucleic acid material, after denaturation, to hybridize to the probe, attached to the solid surface, to form a double stranded complex, which is detected to indicate the presence of the nucleic acid molecule in the sample.

Stated differently, the method comprises amplifying a nucleic acid molecule, in a sample, by use of two primers in a polymerase chain reaction in the presence of a single stranded nucleic acid probe complementary to said molecule, to produced amplified nucleic acid material, wherein said probe is attached to a solid surface by a dendron, allowing said amplified nucleic acid material, after denaturation, to hybridize to said probe to form a double stranded complex, and detecting said complex.

The use of a cell or tissue containing sample in an amplification reaction, such as PCR, may be performed by any means known to the skilled person. There have been various attempts to amplify gene sequences of interest directly from cells and tissues (Chen, S and Evans, G A, Biotechniques 8:32-33, 1990; Ohhara, M. et al. Biotechniques 17:726-728, 1994). As one non-limiting example, Novagen described buffer mixtures that allows direct PCR of blood samples. The Novagen mixtures include BLOODDIRECT™ buffer 1 and BLOODDIRECT™ Buffer A (for human blood), or BLOODDIRECT™ Buffer B (for mouse blood), are mixed with deoxynucleotides, primers, Taq thermostable DNA polymerase, anticoagulant, and a blood sample for successful amplification of a desired DNA sequence by PCR (see Novagen User Protocol TB404). Similar approaches can be used for direct PCR from other cell types and also from tissues.

Non-limiting examples of other cell types as the source of a nucleic acid molecule (DNA or RNA) for use in the disclosed invention include those of a human patient or animal subject as well as plant cells, lower eukaryotic cells, non-eukaryotic cells, and prokaryotic cells. The cells may be present in a variety of possible samples, including a biological fluid like blood, serum, saliva, urine, and saliva; a water, air, or soil sample from the environment; a clinical specimen; and a forensic sample. In other embodiments, the nucleic acid molecule to be detected is in a cell-free form. Non-limiting examples include nucleic acid molecules in a virus or viral particle, such as an RNA virus or viral particle.

In some embodiments, the invention provides a method for detecting a nucleic acid molecule in a sample by use of an immobilized probe as the "capture probe." The method may comprise amplifying a nucleic acid molecule, in a sample, by the polymerase chain reaction (PCR) in the presence of a single stranded nucleic acid probe complementary to the nucleic acid molecule (along with a second nucleic acid primer for PCR), to produced amplified nucleic acid material. The probe (or "capture probe") is directly or indirectly immobilized, or otherwise attached to a solid surface, through its 3' end by a dendron or other structures such as a silanated surface with functional end group of amine, aldehyde, epoxy, etc. for attachment of a nucleic acid probe. In some embodiments, the probe sequence is complementary to the sequence at the 5' end of a strand synthesized during PCR.

After amplification, the amplified nucleic acid material is allowed, after denaturation, to hybridize to the immobilized probe to form a double stranded complex. The complex can then be detected and analyzed by any suitable means known to the skilled person.

In other embodiments, a gene amplification reaction such as PCR is conducted in a chamber (on a chip slide) containing an area of capture probes immobilized on top of dendrons or another chemical structure. Subsequent hybridization is carried out in the same chamber. The slide is washed, scanned, and the results analyzed. In further embodiments, a biological sample is added to a PCR mixture, and the mixture is added to a chamber (of a chip slide) assembled on an area that contains capture probes immobilized on dendrons or another chemical structures. The capture probes are directly or indirectly linked to a solid support, such as a dendron, through the 3' end of the probes. After PCR, hybridization with the capture probes proceeds without any further treatment. Following hybridization, the slide is washed and scanned, and the results are analyzed.

The cells of a sample used in a disclosed method are optionally lysed or permeablized by means known to the skilled person to facilitate the amplification reaction. Non-limiting examples include a detergent, like NP-40 (also known as NP40 or Nonidet P40), to lyse cells and deoxycholate to permeablize cells. The in situ methods used for PCR on tissue slices may also be adapted and used. In alternative embodiments, cells may be ruptured by simply heating them at a high temperature, such as by heating in a microwave as a non-limiting example.

As described above, a combination of direct gene amplification from cells and gene amplification on the surface of capture probes on a gene chip makes "one step diagnosis of gene" possible via a gene chip.

Probe as PCR Primer

In another aspect, the invention provides methods for PCR based amplification with an immobilized probe as one of the primers used in PCR-based amplification. The capture probes linked to solid support can participate in PCR as a primer as long as the 3' end of the probe is available as a primer for chain elongation. A reaction mixture is assembled as described above that is composed of a template DNA, such as cellular DNA or cDNA, an immobilized probe (capture probe on glass slide or chip) for use as a first primer, a second primer for synthesis of the DNA strand complementary to the strand synthesized by the probe as first primer, deoxynucleotide triphosphates, a detectably labeled deoxynucleotide triphosphate, and thermostable DNA polymerase.

Thus the disclosed invention also includes a method for detecting a nucleic acid molecule, in a sample, in the presence of a single stranded nucleic acid probe complementary to said molecule, wherein said probe is attached to a solid surface by a dendron. If the nucleic acid molecule is double-stranded, the probe is complementary to one strand of the molecule. The probe also comprises a sequence for use as one of the primers in a polymerase chain reaction (PCR) to amplify the nucleic acid molecule.

The method may be used to amplify a nucleic acid molecule, in a sample, by the polymerase chain reaction (PCR) using the probe as one of the PCR primers to produce double stranded nucleic acid material attached to the solid surface, which material is detected to indicate the presence of the nucleic acid molecule in the sample.

Stated differently, the method comprises amplifying a nucleic acid molecule, in a sample, by the polymerase chain reaction in the presence of a single stranded nucleic acid probe complementary to said molecule, wherein said probe is attached to a solid surface by a dendron and said probe comprises a sequence for use as one of the primers in said polymerase chain reaction, to produce double stranded nucleic acid material attached to said solid surface, and detecting said double stranded nucleic acid material.

PCR is conducted and the chip slide is washed and scanned by a laser scanner and the result is analyzed. This process is ideal in that a separate hybridization step is unnecessary, thus shortening the steps involved in use of a DNA chip. When combined with PCR of a gene sequence of interest directly from cells, direct analysis of the fluorescently labeled amplified DNA hybridized to capture probes will speed up the gene analysis by a DNA chip. The use of a dendron coated surface, or other surface structure that maintains desired spacing between capture probes, and also use of heat-stable linkage between the capture probes and dendrons, or other structures, are advantageously applied to the successful PCR on the surface of DNA chip. For example, the dendron described by Korean patent 10-0383080-0000 and published U.S. Patent Application 2005/0037413 is suitable for use as described herein.

In some embodiments, the invention includes a method for detecting a nucleic acid molecule in a sample by using an immobilized probe as a primer for nucleic acid synthesis. The method may comprise amplifying a nucleic acid molecule, in a sample as described herein, by the polymerase chain reaction in the presence of a single stranded nucleic acid probe complementary to the nucleic acid molecule, wherein the probe is attached to a solid surface by a dendron or other material as disclosed herein. The probe comprises a sequence for use as one of the primers in the polymerase chain reaction. Chain elongation or extension of the probe produces a double stranded nucleic acid material attached to the solid surface. The attached amplified material may then be detected as described herein.

In other embodiments, gene amplification such as PCR can be conducted in a chamber (on a chip slide) that contains an area of capture probes immobilized on top of dendrons or another chemical structure through the 5' end of the probes. The capture probes are used as one of the two primers needed for PCR. After washing, the slide is scanned, and the results are analyzed. In further embodiments, a biological sample, such as cells, is added to PCR mixture, and PCR is carried out in a chamber (of a chip slide) that contains an area of capture probes immobilized on top of dendrons or another chemical structure. PCR is carried out using the capture probes as one of the two primers needed for PCR. After washing, the slide is read by a confocal laser scanner and the results are analyzed. Again, the cells may be lysed or permeablized as described herein.

Without being bound by theory, and provided to improve the understanding of the invention, one spot on a chip as described herein contains about $10^{11}$ probe molecules and if the PCR reaction is conducted in a volume of 100 µl, each spot contributes about $10^{-8}$ M of probes. This is equivalent to the amount of primers normally used in PCR.

Sequential Amplification and Hybridization

In a further aspect, the invention includes methods wherein the amplification reaction is conducted without the presence of an immobilized probe on a solid substrate. In some embodiments, the methods may be considered to comprise consecutive PCR and hybridization reactions. These methods may be advantageously used where particular conditions, such as salt concentrations or ionic strength, are needed in allowing hybridization to an immobilized probe on a solid substrate, such as a chip, slide, or chamber, of the invention. The amplification reaction may be performed in a separate vessel or container, such as a tube or microfuge tube, or a well, such as a well of a plate or microtiter plate.

After amplification, the reaction volume is transferred, preferably without additional manipulation such as purification or isolation steps or with a minimum amount of handling, to contact an immobilized probe on a solid substrate of the invention. Optionally, the solid substrate may comprise two different, and non-complementary, probes to hybridize to both strands of the amplified material. The composition of the reaction volume may also be adjusted as part of the transfer. Non-limiting examples of such adjustment include addition of concentrated salt solution(s), or dilution of the reaction volume, to alter salt concentration or ionic strength prior to hybridization to the immobilized probe.

Alternatively, an isolation or purification of material from the reaction volume precedes the transfer to contact a probe. This may be advantageously used to remove, or lower the levels of, substances which may interfere in the hybridization reaction. Non-limiting examples of isolation or purification include extraction of proteinaceous material, isolation of amplified polynucleotides, or precipitation of the amplified polynucleotides.

Hybridization to immobilized probes is facilitated by converting the amplified nucleic acid material in the reaction volume to a single stranded form. The conversion may be by denaturation of double stranded material before, or after, the transfer of the reaction volume (and any optional adjustments to the volume). In some embodiments, the denaturation is by the use of increased temperature, such as after transfer, by heating the solid substrate. After heating to denature double stranded nucleic acids, the temperature of the solid substrate may be lowered, optionally in a controlled manner, to allow hybridization to occur.

Thus the disclosed invention also includes a method for detecting a nucleic acid molecule, in a sample, by first amplifying the molecule by PCR and then hybridizing it to a probe containing solid substrate as described herein. In some embodiments, the amplification of the molecule is used to produce amplified nucleic acid material that is then contacting or transferring to a solid substrate comprising a single stranded nucleic acid probe, attached to the solid substrate by a dendron. The probe is complementary to one strand of the molecules in the amplified material. Alternatively, the solid substrate may comprise more than one probe that are complementary to both strands of the molecules in the amplified material. The sequences of the more than one probes may be selected or designed to not be complementary, or not interfere with each other in hybridizing to the amplified material. Optionally, the amplified material is denatured before the contacting or transferring. Alternatively, the amplified material is denatured after the contacting or transferring.

The amplified nucleic acid material is then allowed to form a double stranded complex with said probe, and the complex is detected to indicate the presence of the nucleic acid molecule in the sample.

Stated differently, the method comprises amplifying a nucleic acid molecule, in a sample, by the polymerase chain reaction to produced amplified nucleic acid material, contacting or transferring said amplified nucleic acid material with a single stranded nucleic acid probe complementary to said molecule, wherein said probe is attached to a solid surface by a dendron, allowing said amplified nucleic acid material to form a double stranded complex with said probe, wherein said nucleic acid material is denatured before or after said contacting or transferring, and detecting said complex.

Embodiments of these methods include a combined direct PCR and hybridization assay having the following: (1) slide; (2) the slide coated with dendrons or other chemicals; (3) capture probes linked to the dendrons or other chemicals through the 5' or 3' ends of the probes, (4) a chamber assembled around an area that contains the linked capture probes, (5) adding biological sample to a PCR reaction mixture, (6) performing PCR and hybridization consecutively such that the PCR reaction products are transferred to the chamber.

In other embodiments, a gene amplification reaction such as PCR is carried out in a vessel, and the reaction mixture, without prior purification of the reaction mixtures, is transferred to a chamber, such as one on a DNA chip slide, containing an area of capture probes immobilized through dendrons or another chemical structure. Hybridization is then conducted. The slide is washed, scanned, and the results analyzed.

Exemplification of Features

The disclosed chips and slides are non-limiting examples of solid support substrates which may be used in the practice of the invention. Any suitable solid support material may be used. Non-limiting examples include substrates such as oxidized silicon wafer, silica, fused silica, and glass slide.

A dendron which is coated on the surface of substrate in this invention is a kind of dendrimer. Dendrimers are highly branched polymers with uniform size and molecular weight as well as a well-defined structure. They consist of a central multifunctional core, multifunctional repeating unit attached around the core, and a terminal or end group. According to their shape, they are divided into two types. The first one has a circular or elliptic shape of which repeating units are regularly stretched from a core, whereas the second type has a conic shape of which repeating units are directionally stretched from a core. The second type is generally called as dendron.

Dendrons having nine branches are mainly used to exemplify the modification of a surface of a solid substrate in this invention. The dendron, N-Cbz-[1]amine-[9]acid, described in Oh, S. J. et al, *Nucl. Acid Res.* 2005, 33(10), e90 (and published U.S. Patent Application 2005/0037413) is a non-limiting example of a dendron that may be used.

This dendron molecule was designed for efficient immobilization via covalent binding to the substrate, facile deprotection, intact reactivity of the amine at the apex (of the conical shape), and low nonspecific binding of oligonucleotide or polynucleotide. Various biological molecules as a nucleic acid probe may be attached to the amine group at the apex of a dendron. Non-limiting examples of attached molecules include polynucleotides, oligonucleotides and PCR products.

As reported in Korean patent 10-0383080-0000 and published U.S. Patent Application 2005/0037413, the amines at the apex of among dendrons maintain mesospacing. Therefore, the biological molecules linked to each amine will also maintain mesospacing thus reducing steric hinderance among the biological molecules. In some embodiments, the dendrons on a substrate may be spaced at regular intervals, such as that of about 0.1 nm, about 10 nm, or about 100 nm. As a result, the probes immobilized via the dendrons are also spaced at regular intervals. This also results in dramatic reduction of noise in the analysis of gene sequences by DNA chip (see Oh as cited above).

In addition to the dendron described above, other dendrons with different numbers of branches may also be used in the practice of the disclosed invention. Non-limiting examples include a dendron with from about 3 to about 27 branches.

Also, other chemical structures that allow immobilization of biomolecules at the apex of cone shaped polymers can be used for the direct and consecutive gene amplification and hybridization described above. The immobilization may be via a covalent bond that is readily cleaved so that the immobilization is reversible.

Immobilized Polynucleotides

The biomolecules used for the combined gene amplification and hybridization described in this invention include capture probes of single-stranded polynucleotides, such as DNA, of about 15 to about 70 nucleotides in length that are sufficiently complementary to the nucleic acid (DNA or RNA) sequences in biological samples to be analyzed. The nucleic acid (DNA or RNA) sequences that are sufficiently complementary to the capture probes may be any regardless of the source.

In some embodiments, a capture probe comprises a sequence that is unique to a molecule amplified from a sample described herein. The sequence may contain at least about 16, at least about 18, at least about 20, at least about 22, at least about 24, at least about 26, at least about 28, at least about 30, or at least about 32 consecutive basepairs of a sequence that is not found in other molecules present with the amplified molecule. Other embodiments are polynucleotides of at least or about 50, at least or about 100, at least about or 150, at least or about 200, at least or about 250, at least or about 300, at least or about 350, at least or about 400, at least or about 450, or at least or about 500 consecutive bases of a sequence that is not found in other gene sequences. The term "about" as used in the preceding sentence refers to an increase or decrease of 10% from the stated numerical value. Alternatively, a polynucleotide probe may contain minor mismatches (e.g. via the presence of mutations) which do not affect hybridization to the nucleic acids of a sample.

The probe sequence may be to either strand of a double-stranded sequence. A probe may thus hybridize to the "coding" or "non-coding" strand of a double-stranded sequence. Alternatively, and in the applicable cases, a probe may hybridize to the "+" or strand of a nucleic acid sequence as understood by the skilled person.

Preparation of Solid Medium

Coating of a solid substrate or medium, like a glass slide or microarray, with dendron may be by a suitable means known to the skilled person. As a non-limiting example, the substrate is first coated with dendron, and capture probes are linked to the apex of the dendron. The coating may be to prepare surfaces on the substrate or medium for immobilization of a polynucleotide probe or primer as described herein.

In some embodiments, the surface is that of a "microarray", which refers to a linear or two-dimensional or three dimensional (and solid phase) array of discrete surface regions. Each region has a defined area that is formed on the surface of a solid support such as, but not limited to, glass, plastic, or synthetic membrane. In some cases, each region is a surface of a chamber as described herein. The density of the discrete regions on a microarray may be determined by the total number of immobilized polynucleotides to be detected on the surface of a single solid phase support, such as of at least about $50/cm^2$, at least about $100/cm^2$, or at least about $500/cm^2$, up to about $1,000/cm^2$ or higher. An array may contain less than about 500, about 1000, about 1500, about 2000, about 2500, or about 3000 regions of immobilized polynucleotides in total. Because the position of each particular group of probes in the array is known, the identities of a sample polynucleotides can be determined based on their binding to a particular position in the microarray. As an alternative to the use of a microarray, an array of any size may be used in the practice of the invention.

The regions may be in the form of spots with a diameter of about 100 to about 500 µm, such as about 200 to about 300 µm or about 240 µm. While each region generally contains one probe type with the same sequence, several regions with the same probe type may be on the same solid surface. This allows the same probe type to be used in parallel assays. In some embodiments, the regions may be spaced apart from each other by about 100 to about 500 µm, such as from about 200 to about 300 µm or about 280 µm.

The process of coating dendron is as follows. The substrate such as glass slide is washed and dried. The washed slide is dipped into silane solution to form a silanated surface. After silanation, the substrate is washed with an appropriate solvent and dried. The silanated substrate is then dipped into a solvent containing dendron such as N-Cbz-[1]amine-[9]acid and maintained under nitrogen (N2) gas.

In the case of N-Cbz-[1]amine-[9]acid, the amine is protected. Therefore, the protective group is removed to expose the amine moiety. After deprotection, the substrate surface is washed with solvent such as methanol. For crosslinking of either the 3' end or 5' end of a capture probe to the exposed dendron amine, the deprotected dendron surface is modified with di(N-succinimidyl)carbonate (DSC). After the substrate is washed with deionized water, capture probe is dissolved in a buffer solution and spotted on a DSC-modified dendron substrate, and reacted for 12 hours under humidity of 85%.

A sealed chamber is constructed that includes the area of the capture probes, and consecutive gene amplification and hybridization is carried out in this chamber. The assembly of the chamber(s) may be on a chip slide. The chamber can be assembled by use of commercially available material (for example, HYB-SEAL™ Incubation Chambers, Bio-Rad Laboratories). The chamber assembly material is taped on an area of the chip slide that contains the capture probes immobilized on the surface of dendrons. After sample solution for gene amplification is added to the chamber, the top of the chamber is sealed with a cover.

PCR

As described herein, some methods of the invention may be practiced by use of direct PCR. For direct PCR, biological materials such as cells, appropriate primers, deoxynucleotide triphosphates, a fluorescent labeled deoxynucleotide triphosphate, appropriate buffer, and thermostable DNA polymerase are premixed. The mixture is added through an injection hole of a chamber that contains an area of capture probes immobilized on the surface of dendrons. PCR is performed in a temperature cycler that can accept slides (For example, PTC Slide Cycler, MJ Research, Co.).

In the case of direct PCR with the capture probes as primers, the capture probes will be linked to dendron through 5' end of the DNA. After PCR, the chamber assembly may be pilled off from the glass slide, and the slide is washed and/or rinsed before being scanned by a confocal laser scanner as described below.

General principles for the determination of PCR temperatures, cycle times, and numbers of cycles are known to the skilled person. As a non-limiting example, the temperature requirements for PCR may be as follows: the temperature range for DNA denaturation (strand separation) is 90-95° C., the temperature for annealing of primers with separated strands of DNA is between 50-65° C., and finally the optimum temperature for elongation of DNA chain from the annealed primer by thermostable DNA polymerase is 70-75° C.

Hybridization Conditions

For hybridization, the temperature for denaturation of PCR product is 90-95° C., and the range of temperature for hybridization of PCR product with the capture probes linked to dendrons is 40-65° C.

In the case of consecutive direct PCR and hybridization, the capture probes will be linked via their 3' ends to the dendrons. After direct PCR with biological samples such as cells, the PCR reaction mixture (in a chamber on a glass slide) may be heated at about 95° C., and hybridization may carried out for about one hour at about 50° C. and about 2 hours at about 45° C., all conditions as non-limiting examples. After hybridization, the chamber is removed and the slide is washed once with 1×SSC+0.1% SDS, once with 0.1×SSC+0.1% SDS and once with 1×SSC, all as non-limiting examples.

Alternatively, the hybridization conditions used may be at a temperature of about 30 to about 80° C., such as from about 40 to about 70° C. or from about 55 to about 65° C. The hybridization temperature may be adjusted as deemed appropriate by the skilled person based on multiple factors, such as the melting temperature of the probe sequences used. The temperature may also be determined, adjusted, and held relatively constant for each hybridization reaction.

The cycling of temperatures in the practice of the instant invention may be by any means known to the skilled person. In some embodiments, a solid substrate, with immobilized capture probes on a surface, of the invention is in operative contact with a thermocycler capable of regulating the cycling parameters in the solid substrate. Non-limiting examples of such parameters include temperature, temperature cycle times, and number of temperature cycles. Various thermocyclers are known to the skilled person, including those which are automatic or semi-automatic after selection of cycling parameters like those described above.

Detection Means

While many of the amplification reactions described herein labels the amplified nucleic acid material by inclusion of a fluorescently labeled deoxynucleotide triphosphate in the reaction mixture, other labeling means may be used. One non-limiting example is the use of a radioisotope label. Alternatively, other means may be used to detect the amplified nucleic acid material after immobilization as described herein. Non-limiting examples include electrochemical detection and the use of a double stranded nucleic acid binding agent, such as SYBR® Green, which is advantageously used after a wash or rinse step to remove unbound material from a chip or slide surface.

Alternative detection means known to the skilled person may also be used. Non-limiting examples beyond fluorescence include labeling with a radioactive or chemoluminescent moiety or other means based upon a chemical, enzymatic, physico-chemical or antigen-antibody binding process. In some embodiments, a label such as alkaline phosphatase, horseradish peroxidase, β-galactosidase, urease, luciferase, rhodamine, fluorescein, phycoerythrin, luminol, isoluminol, an acridinium ester or a fluorescent microsphere is used as a detectable moiety.

The analysis of the amplified material on a solid substrate may be by any suitable means known to the skilled person. For DNA analysis after hybridization, a general, non-limiting procedure to be followed is by using a commercially available confocal laser scanner for image acquisition and a quantitative microarray analysis software for the fluorescence intensity analysis. The invention is not limited to use of a particular analysis method. In a fluorescence intensity analysis method as a non-limiting example, PCR product is labeled with fluorescence by carrying out chain elongation in the presence of deoxynucleotide triphosphate labeled with fluorescent group. One then determines the level of fluorescence that hybridized to capture probes after hybridization by a laser scanner and computer microarray software analyzes the signals on a DNA chip slide.

Range of Nucleic Acid Molecules Detected

As evident from the above, the disclosed methods may be practiced to detect a nucleic acid molecule of interest in a sample. The nucleic acid molecule may be a genomic DNA molecule, a mitochondrial DNA molecule, or an episomal DNA molecule. In other embodiments, the nucleic acid to be detected is an RNA molecule, such as an mRNA molecule, which may be reverse transcribed to form a single or double stranded cDNA which is then used in the methods of the invention. In some embodiments, the RNA molecule is from a eukaryotic cell, a non-eukaryotic cell, or a virus or viral particle.

Means to reverse transcribe RNA are known to the skilled person. Non-limiting examples include use of an poly-dT or oligo-dT containing primer for polyadenylylated RNA and use of a sequence specific primer to prime synthesis of the first cDNA strand complementary to a single stranded RNA.

It is also possible to synthesize a duplex of RNA and the complementary cDNA strand in whole cells. A non-limiting means includes adding 1% NP-40 to a reaction mixture for 1st strand cDNA synthesis. To reduce the danger of gene amplification of genomic DNA, various means may be used, including selection of primers complementary to RNA sequences, such as those at splice junctions, not found in genomic DNA; use of RNase-free DNase treatment; and use of primers for reverse transcription that contain unique sequences that are complementary to primers used for PCR.

Where RNA copy number is high, there may be no need for the amplification of the reverse transcribed RNA. The first strand DNA may be labeled with reagents as described herein in lysed whole cells and hybridization with capture probes on surface of dendron can be carried out. Synthesis of 1st strand cDNA in whole cells was recently published (see Keays, K M et al. Laser capture microdissection and single-cell RT-PCR without RNA purification *Journal of Immunological Methods* 302 (2005) 90-98). First strand cDNA synthesis was carried out in a reaction mixture containing 1% NP-40 to lyse cells. NP40 did not affect the cDNA synthesis. Cells containing the cDNA may then be used in a disclosed method as described herein.

When presence of an RNA virus such as HIV, HCV, avian flu virus, and others is to be detected or determined, then one step RT-PCR can be carried out with whole cells or blood samples on top of capture probes and hybridization can be carried out as described herein. Invitrogen sells reaction mixtures for one step RT-PCR (Cat No. 12574-018).

If low copy number RNA is investigated, the cells may be lysed, and DNA digested before use. The sample is transferred to a chamber on a slide followed by one step RT-PCR and hybridization as described herein.

Whether DNA or RNA is to be detected, the nucleic acid molecule may be that of a pathogen, including bacterial, viral, or lower eukaryote in character. In other embodiments, the nucleic acid molecule to be detected comprises a mutated sequence and the immobilized probe is complementary to that sequence. This may be advantageously used to detect genetic diseases comprising a mutation in a subject's DNA.

Kits

The invention further provides kits for the amplification and detection of nucleic acid molecules as described herein. A kit will typically comprise one or more reagents to detect reference gene expression as described herein for the practice of the present invention. Non-limiting examples include polynucleotide primers for amplification, one or more enzymes used in the methods of the invention, and one or more tubes for use in the practice of the invention. In some embodiments, the kit will include an array or microarray, or solid media capable of being assembled into an array or microarray, for the detection of amplified molecules as described herein.

A kit of the invention may also include instructional materials disclosing or describing the use of the kit or one or more components thereof in a method as described herein. A kit may also include additional components to facilitate the particular application for which the kit is designed. Thus, for example, a kit may additionally contain means of detecting a label (e.g. enzyme substrates for enzymatic labels, filter sets to detect fluorescent labels, or the like). A kit may additionally include buffers, salts, solutions, and other reagents recognized for use in a method of the invention.

Having now provided a written description, the same will be more readily understood through reference to the following examples which are provided by way of illustration, and are not intended to be limiting of the disclosure, unless specified.

EXAMPLES

Example 1

Preparing DNA Microarrays

Figure 3:
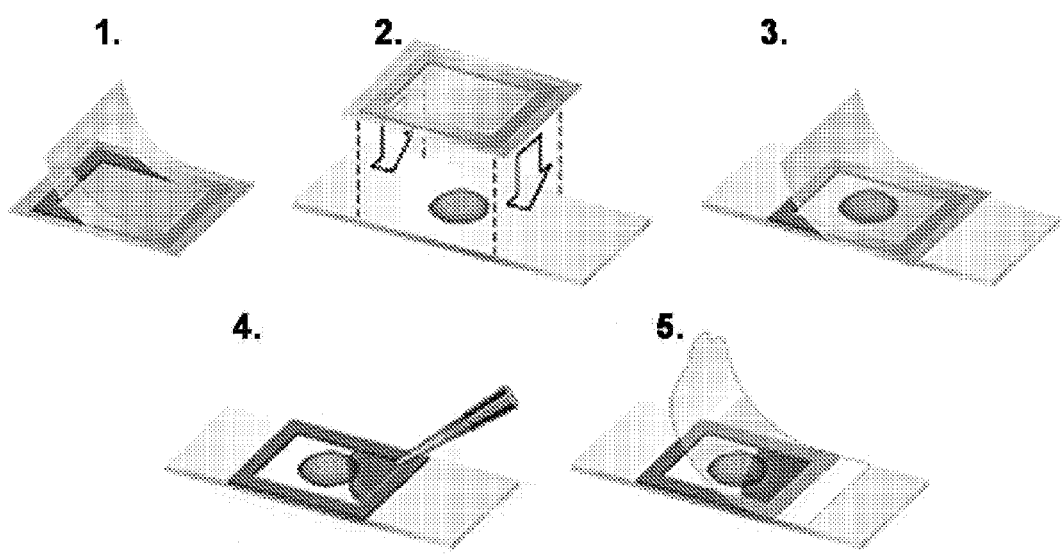
FIG. 3 shows a Hybrid Chamber with 25 μL Frame-Seal chambers (MJ research).

3' or 5'-Amine-tethered capture probe oligonucleotides were immobilized on a DSC-activated dendron-modified surface of the glass slide by spotting the solution in a buffer containing 25 mM sodium bicarbonate, 5 mM MgCl$_2$ and 10% (v/v) dimethyl sulfoxide at pH 8.5 using a Q-Array mini microarrayer (Genetix). After spotting the probe oligonucleotides, the microarray was incubated in a chamber maintained at 85% humidity for overnight to give the amine tethered DNA sufficient reaction time. Slides were then stirred in a buffer solution containing 2×SSPE (0.30 M sodium chloride, 0.020 M sodium hydrogen phosphate and 2.0 mM EDTA), pH 7.4 and 7.0 mM SDS at 37° C. for 1 h to remove non-specifically bound oligonucleotides. Finally, the DNA-functionalized microarray was dried under a stream of nitrogen. See FIG. 3, which schematically illustrates the Hybrid Chamber (25 µL Frame-Seal chambers (MJ research)).

Example 2

Blood-direct PCR and Hybridization on the Dendron Surface

5 µl of blood was microwaved for 3 minutes or heated at 99° C. for 10 min in 0.2 ml PCR tubes with tightly fitting caps. The sample was centrifuged at >1500 rpm for seconds, and 0.5-1 µl of supernatant was added to PCR reaction mixture. In the case of genomic DNA, it was extracted from HEK 293 cell using GENE ALL™ Blood SV mini kit and added to PCR reaction mixture. The solutions were transferred onto the dendron surface to which capture probe oligonucleotides (DNA sequence 5'-TCGACATAGTNTGGTGGTGCC-NH$_2$-3' where N is G(wt), A, T, or C (mt), SEQ ID NO: 1) were immobilized. PCR and hybridization reactions were consecutively performed using a Px2 thermal in situ slide cycler (Thermo).

For gene amplification directly from blood samples, 5 µl of blood was heated in a microwave oven for 3 minutes or heated at 99° C. for 10 min in a 0.2 ml plastic conical tube with tightly fitting caps. The sample was centrifuged at >1500 rpm for seconds, and 0.5-1 µl of supernatant was added to a PCR reaction mixture. For purification of genomic DNA, DNA was extracted from HEK 293 cell using GENE ALL™ Blood SV mini kit and added to a PCR reaction mixture (25 µl).

The forward primer in the PCR reaction has a sequence represented by 5'-TAC TCC CCT GCC CTC AAC AA-3' (SEQ ID NO: 1) while the reverse primer has a sequence represented by 5'-CTG GAG TCT TCC AGT GTG ATG AT-3' (SEQ ID NO: 2).

The reaction mixture was transferred into the chamber assembled on the dendron surface comprising spots with immobilized capture probe oligonucleotides surrounding codon 216 in p53 gene (DNA sequence 5'-TCGACATAGT-NTGGTGGTGCC-NH$_2$-3' where N is G for the wild type codon 216, and A, T, or C is a mutant codon 216, SEQ ID NO:3). Each spot contained one of the four possible oligonucleotides. PCR and hybridization reactions were consecutively performed using a Px2 thermal in situ slide cycler (Thermo).

Figure 4:
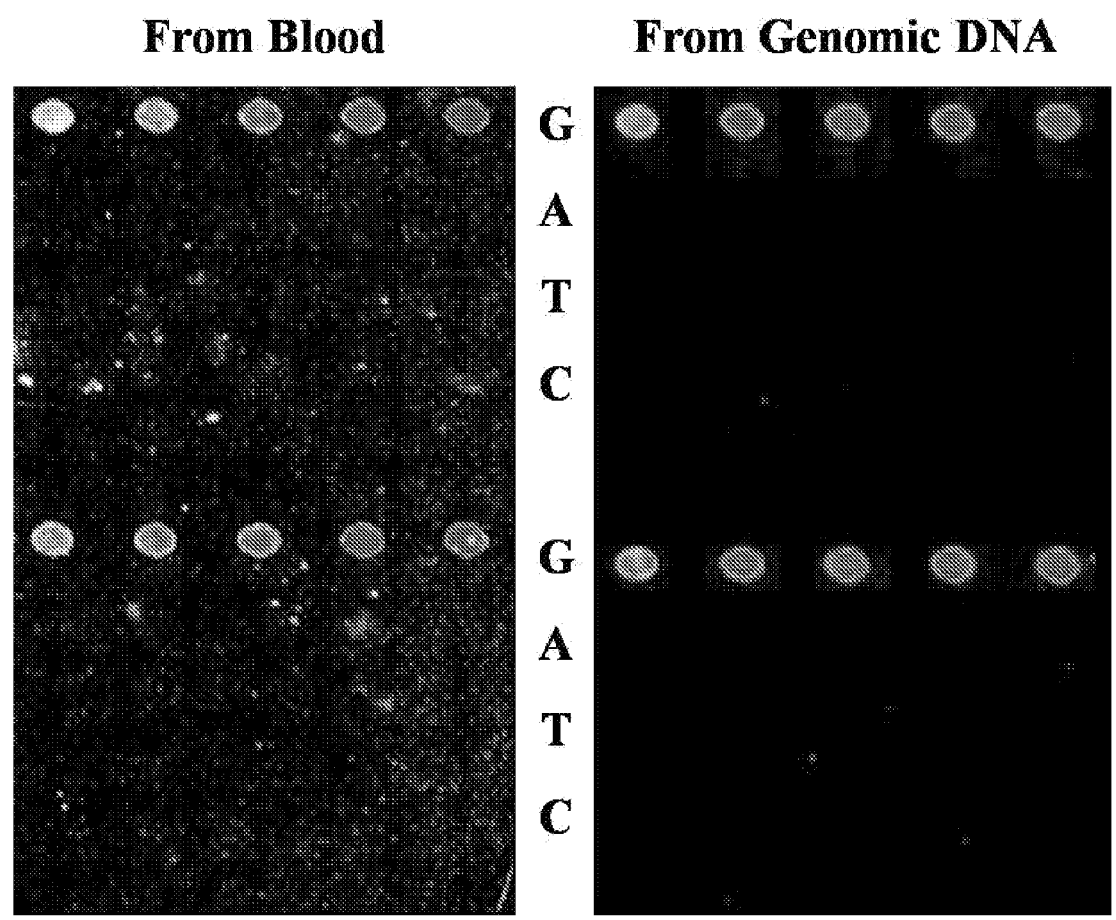
FIG. 4 shows the fluorescence image obtained after consecutive reactions of PCR of blood (left) or genomic DNA (right) and hybridization on the dendron surface for detecting codon. 216 in the p53 gene.

The PCR conditions were as follows: 85-95° C. for 10 minutes, 40-60 cycles at 85-95° C. for 30 s, 50-55° C. for 30 s, 70-75° C. for 30 s, with a final extension at 70-75° C. for 7 minutes. The hybridization conditions were as follows: heating at 90° C. for 5 min followed by incubation at 25° C. for 2 hours. See FIG. 4 for results, which show the fluorescence image obtained after consecutive PCR and hybridization of blood (left) or genomic DNA (right) on the dendron surface. The arrays of capture probes with the four possible sequences were duplicated.

Example 3

Serum Based PCR and Hybridization Using Fluorescence Labeled Primers

Capture Probes

The probes were designed to determine the nucleotide sequences at position 1896 (G versus A) in the HBV (Hepatitis B virus) genome. The capture probes for detection of codon 1896-wild type (5'-GGT TTG GGG CAT GGA CAT T-NH$_2$-3', SEQ ID NO:4) and 1896-mutant type (5'-GGT TTA GGG CAT GGA CAT T-NH$_2$-3', SEQ ID NO:5) from the HBV genome were attached on the dendron surface.

Serum Based PCR and Hybridization Consecutively on the Dendron Slide on which Capture Probes were Immobilized About 10-20 µl of HBV-infected serum was heated at 99° C. for 10 min on a heating block. The heated sample was then centrifuged, and 2.5 µl of the clear supernatant was added to a PCR solution which contained 10 pmol of fluorescently labeled (Cy3) forward primer (5'-Cy3-TTAAGGACTGG-GAGGAGCTG-3', SEQ ID NO:6) and fluorescently labeled (Cy5) reverse primer (5'-Cy3-GCTCCAAATTCTT-TATAAGGGTCA-3', SEQ ID NO:7), 0.25 mM dNTP mixture, 5 Units of Taq polymerase (Biotools), 1× buffer, and betaine 0.1M in a final volume of 25 µL.

Figure 5:
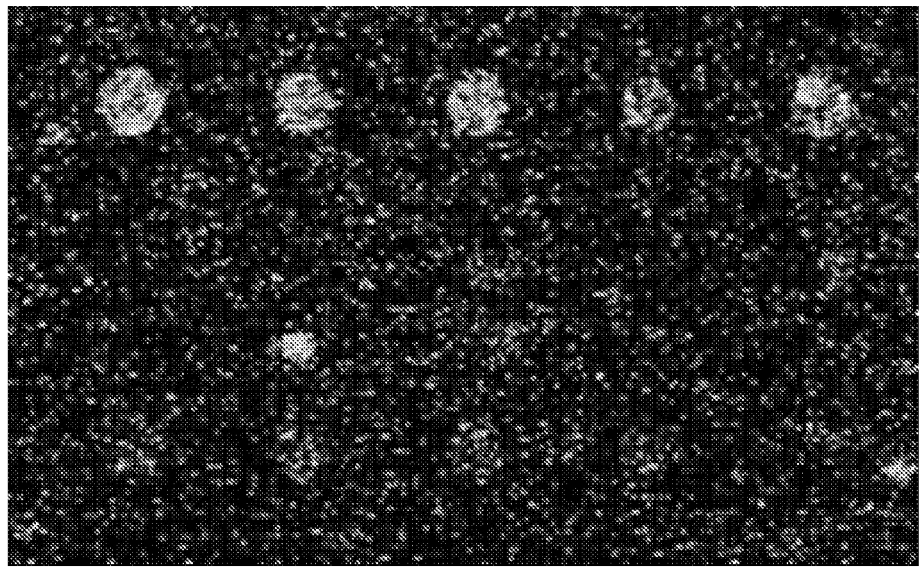
FIG. 5 shows the fluorescence image obtained after hybridization between amplified PCR product of HBV-infected serum and capture probe on the dendron surface with the use of fluorescently labeled primers.

After transferring the above mixture into the chamber assembled on the dendron surface on which capture probes were immobilized, PCR and hybridization reactions were performed consecutively. The PCR conditions were as follows: predenaturation at 85-95° C. for 10 min, 20-60 cycles of incubation at 85-95° C. for 30 s, 50-55° C. for 30 s, 70-72° C. for 30 s, with a final extension at 70-72° C. for 7 min. The hybridization conditions were as follows: heating at 90° C. for 5 min, and incubation at 25° C. for 2 hours. See FIG. 5, which shows the fluorescence image obtained after hybridization between amplified PCR product of HBV-infected serum and capture probe on the dendron surface. Note that PCR of HBV-infected serum and hybridization reactions were consecutively performed on the dendron slide.

Serum Based PCR in Tube and Hybridization on the Dendron Slide on which Capture Probes were Immobilized In this experiment, PCR was performed in a tube, and the resulting PCR product, without purification, was transferred to the dendron surface on which capture probes were immobilized. Hybridization was performed on the dendron surface. The PCR conditions were as follows: predenaturation at 94° C. for 10 min, 40-60 cycles of incubation at 94° C. for 30 s, 55° C. for 30 s, 72° C. for 30 s, with a final extension at 72° C. for 7 min.

Figure 6:
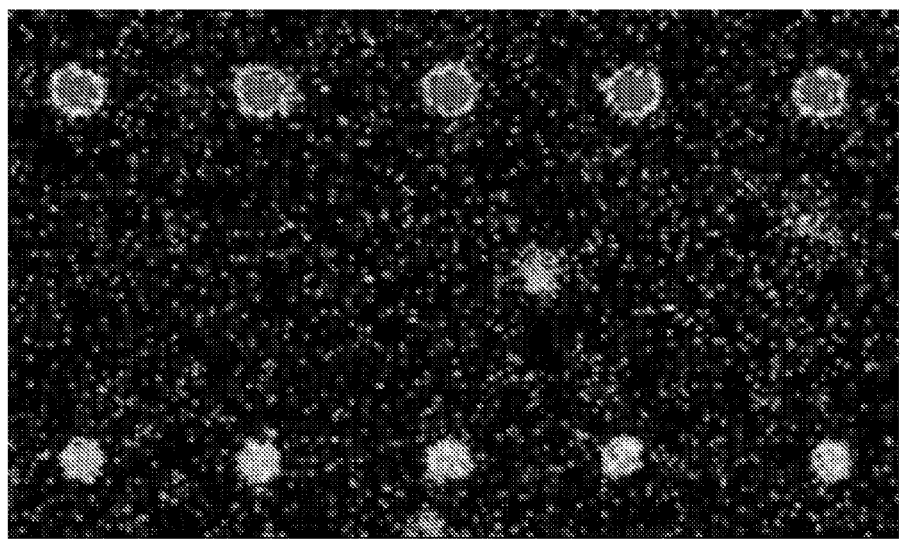
FIG. 6 shows the fluorescence image obtained after hybridization between amplified PCR (in tube) product of HBV-infected serum and capture probe on the dendron surface.

See FIG. 6, which shows the fluorescence image obtained after hybridization between amplified PCR product of HBV-infected serum and capture probe on the dendron surface. PCR of HBV-infected serum was conducted in a tube separate from the slide, and the amplified nucleotide material was transferred without additional manipulation, such as purification or isolation steps, to the dendron surface to be hybridized with capture probe DNAs which were immobilized on the dendron slide.

Example 4

One-step RT-PCR and Hybridization on Slide

Consecutive RT-PCR and Hybridization Consecutively on the Dendron Surface

Total RNA (6 ng) which was extracted and purified from HEK-293 cells was added to one-step RT-PCR mixture (total 25 µl) consisting of 400 nM forward primer (5'-TAC TCC CCT GCC CTC AAC AA-3', SEQ ID NO:1), 400 nM reverse primer (5'-CTG GAG TCT TCC AGT GTG ATG AT-3', SEQ ID NO:2), low dTTP-dNTP mixture (200 µM dATP, 200 µM dGTP, 200 µM dCTP and 100 µM dTTP), 100 µM Cyanine3-dUTP, 1× reaction buffer, 1 mM MgSO$_4$, 2.5 units of AMV reverse transcriptase and 2.5 units of Tfl DNA polymerase. The mixture was transferred into a chamber assembled on the dendron surface containing capture probe DNAs immobilized.

Figure 7:
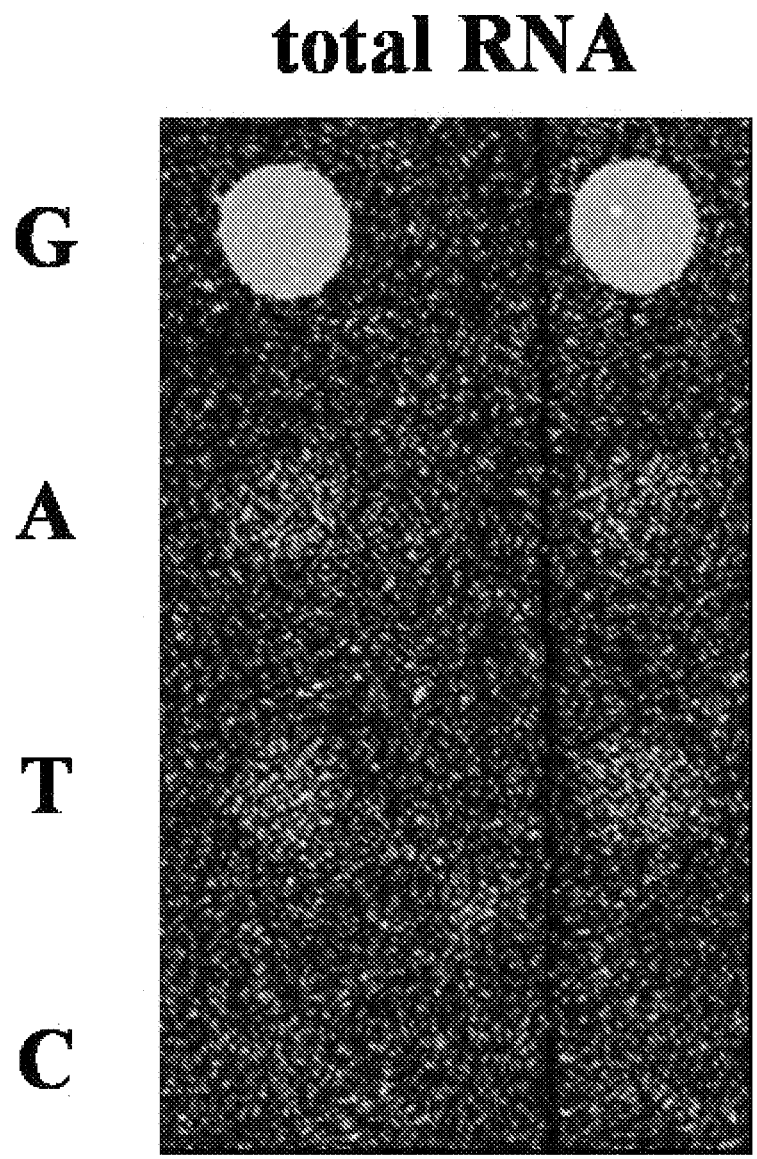
FIG. 7 shows the fluorescence image obtained after consecutive reactions of RT-PCR of total RNA and hybridization on the dendron surface.

RT-PCR and hybridization reactions were consecutively performed using a Px2 thermal in situ slide cycler (Thermo). The RT-PCR was programmed as follows: reverse transcription at 45° C. for 1 hour, RT inactivation and RNA/cDNA/primer denaturation at 94° C. for 2 minutes, subsequent 60 cycles of incubation at 95° C. for 30 seconds, 63° C. for 30 seconds and 68° C. for 60 seconds, followed by a final elongation step at 68° C. for 7 minutes. The hybridization conditions were as follows: 50° C. for 1 hour, 47° C. for 1 hour, and 45° C. for 2 hour. The 3'-amine-modified capture probe oligonucleotide containing codon 216 in the p53 gene was 5'-TCGACATAGTNTGGTGGTGCC-NH$_2$-3' where N is G for the wild type sequence, and A, T, or C is a mutant sequence (SEQ ID NO:3). See FIG. 7, which shows the fluorescence image obtained after consecutive reactions of RT-PCR of total RNA and hybridization on the dendron surface.

Example 5

Genomic DNA or Blood-direct PCR in Tube, and Transferring the Amplified Materials without Purification to the Dendron Surface for Hybridization The capture probes were as follows:
for codon 175 in the p53 gene, 5'-GTTGTGAGGCNCTGCCCC-NH$_2$-3' where N is G for the wild type sequence, and A, T, or C is a mutant sequence, SEQ ID NO:8;
for codon 215 in the p53 gene, 5'-TTTCGACATANTGTGGTGGTG-NH$_2$-3' where N is G for the wild type sequence, and A, T, or C is a mutant sequence, SEQ ID NO:9;
for codon 216, 5'-TCGACATAGTNTGGTGGTGCC-NH$_2$-3' where N is G for the wild type sequence, and A, T, or C is a mutant sequence, SEQ ID NO:3.

Genomic DNA was extracted from HEK293 cell lines and purified with a commercially available kit. Blood was treated via two methods:
1) 10 µl of blood was microwaved for 3 minutes in 0.2 ml PCR tubes with tightly fitting caps. The sample was centrifuged at >1500 rpm for seconds, and 0.5-1 µl of supernatant was added to PCR reaction mixture; and
2) 1 µl of 10% NP-40 (final concentration 1%) was added to 9 µl of whole blood sample in a 0.2 ml plastic tube with tightly fitting caps, and the sample was incubated at room temperature for 5 minute. After incubation, the sample was heated at 99° C. for 10 minute, and then chilled on ice. After a brief centrifugation at >1500 rpm, 0.5-1 µl of the supernatant was added to a PCR reaction mixture.

Genomic DNA or blood treated with microwave or NP-40 was added to PCR solution containing forward primer (TTC AAC TCT GTC TCC TTC CTC TT, SEQ ID NO: 10), reverse primer (GTT ATA GGG AGG TCA AAT AAG CAG, SEQ ID NO:11), low dT-dNTP mixture (final conc. dATP, dGTP, dCTP=100 µM, dTTP=60 µM), Cy3-dUTP(final conc. 30 µM), and 2.5 U Taq polymerase (FASTSTART™ High Fidelity PCR system, ROCHE) in 1×buffer (supplemented with Taq polymerase). The PCR conditions were as follows: 95° C. for 15 minutes, 20-60 cycles at 95° C. for 30s, 53° C. for 30s, 72° C. for 45s, with a final extension at 72° C. for 15 minutes.

Without purification, the PCR product was transferred onto the dendron surface on which the capture probes were immobilized. Hybridization was performed as follows: heating at 95° C. for 5 minutes and then incubation at room temperature for about 2 hours.

Figure 8:
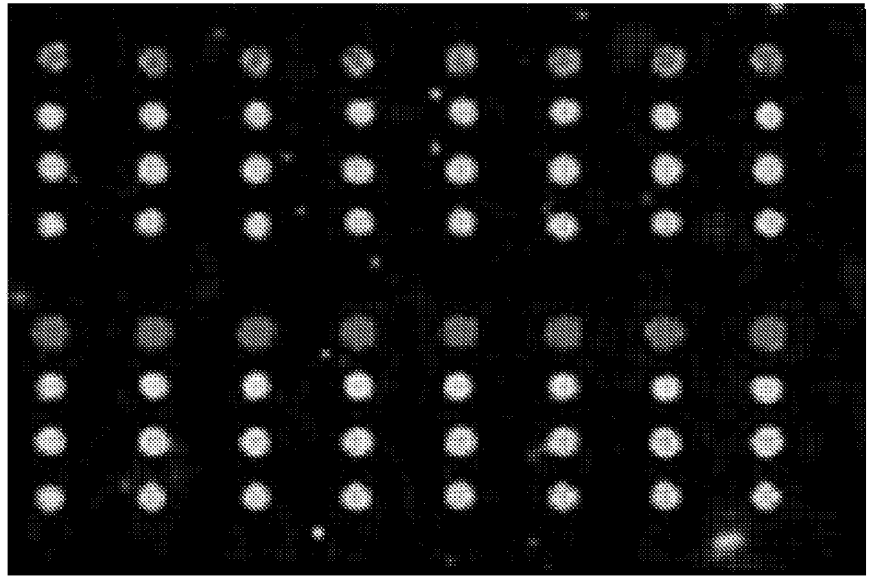
FIG. 8 shows the fluorescence image obtained after hybridization between genomic DNA amplified in a tube (and used directly without additional purification) and capture probe DNAs which were immobilized on the dendron surface for detection of codons 175 and 216 of p53 gene.

FIG. 8 shows the fluorescence image obtained after hybridization between PCR product of gDNA and capture probe DNAs which were immobilized on the dendron surface. The PCR was conducted in a tube, and the amplified product was transferred without additional manipulation, such as purification or isolation steps, to the dendron slide for hybridization. Two capture probes, which can detect codons 175 and 216 in the p53 gene, were immobilized.

Figure 9:
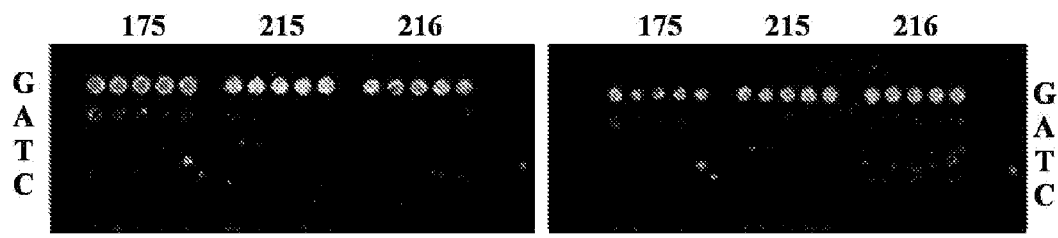
FIG. 9 shows the fluorescence images obtained after hybridization between PCR product of 0.5 μl (left) or 1.0 μl (right) of microwave-treated blood (PCR reaction in tubes used directly without additional purification) and capture probe DNAs which were immobilized on the dendron surface for detecting codons 175, 215 and 216 in the p53 gene.

FIG. 9 shows the fluorescence images obtained after hybridization between PCR product of 0.5 µl (left) or 1.0 µl (right) of microwave-treated blood and capture probe DNAs which were immobilized on the dendron surface. The PCR was conducted in a tube, and the amplified product was transferred without additional manipulation, such as purification or isolation steps, to the dendron slide for hybridization. Three capture probes, which can detect codons 175, 215, and 216 in the p53 gene, were immobilized.

Figure 10:
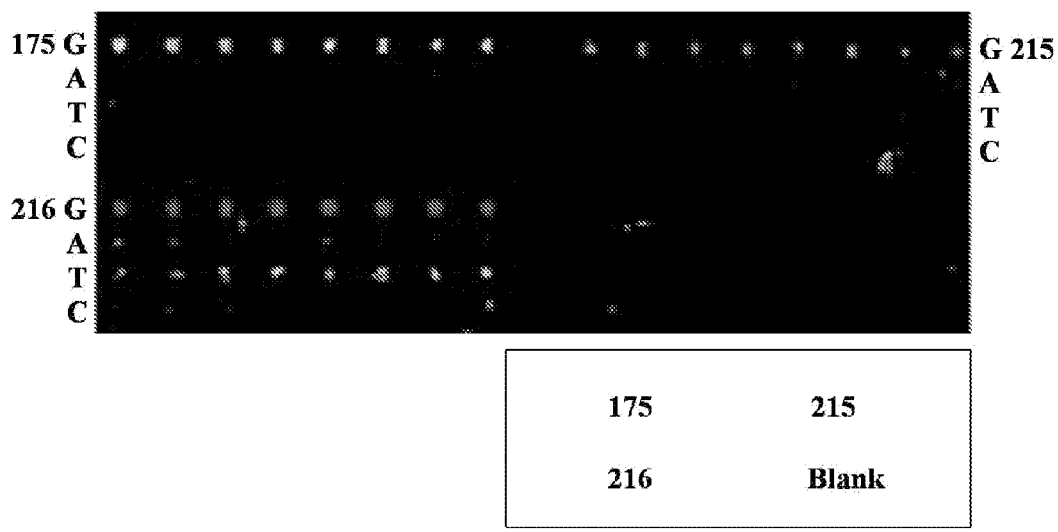
FIG. 10 shows the fluorescence image obtained after hybridization between PCR product of NP-40-treated blood (PCR reaction in a tube used directly without additional purification) and capture probe DNAs which were immobilized on the dendron surface. The positions of the three capture probes used and the blank surface are indicated on the right.

FIG. 10 shows the fluorescence image obtained after hybridization between PCR product of NP-40-treated blood and capture probe DNAs which were immobilized on the dendron surface. The PCR was conducted in a tube, and the amplified product was transferred without additional manipulation, such as purification or isolation steps, to the dendron slide for hybridization. Three capture probes, which can detect codons 175, 215, and 216 in the p53 gene, were immobilized.

Example 6 gDNA, 5'-NH$_2$-capture Probe

The nucleic acid probes immobilized on the chip surface is used as a primer in the amplification of the nucleic acid molecule to be detected. A second primer is used to amplify the nucleic acid molecule. The probe as first primer is used to hybridize with the template nucleic acid molecule to be detected followed by extension of the probe sequence (via a suitable nucleic acid polymerase) to produce a first nucleic acid strand complementary to the nucleic acid molecule being amplified.

Capture Probe Oligonucleotides

For this study, 5'-NH$_2$-modified capture probe oligonucleotides were immobilized on the dendron slide to be used as a (forward) primer in the amplification of the nucleotide sequence to be detected. For analyzing the p53 mutation in codon 248, the immobilized capture probes had the sequences of 5'-NH$_2$GAAACACTTTTCGACATAGTN where N is G(wt), A, T, or C(mt), SEQ ID NO:12).

The reverse primer had the following sequence: 5'-GTT ATA GGG AGG TCA AAT AAG CAG-3', SEQ ID NO: 11.

Genomic DNA Samples 90 ng of genomic DNA sample extracted form HEK 293 cell was added to the PCR mixture which contained a reverse primer or one pair of primers (forward and reverse), low dT-dNTP mixture (100 mM dATP, 100 mM dGTP, 100 mM dCTP and 50 mM dTTP), 50 mM Cyanine3-dUTP (Genechem), and 2.5U Taq polymerase (Roche) in 1× buffer (supplemented with Taq polymerase). The PCR solutions were transferred onto the dendron slide.

PCR Conditions

The PCR conditions were as follows: incubation at 87° C. for 5 minutes, and subsequent 40 cycles of incubation at 87° C. for 30 seconds, 55° C. for 30 seconds, 72° C. for 20 seconds, followed by a final elongation step at 72° C. for 5 minutes.

There was no denaturation of the amplified DNA after PCR and no hybridization step. The slide was washed after PCR without hybridization and read in a scanner.

Figure 11:
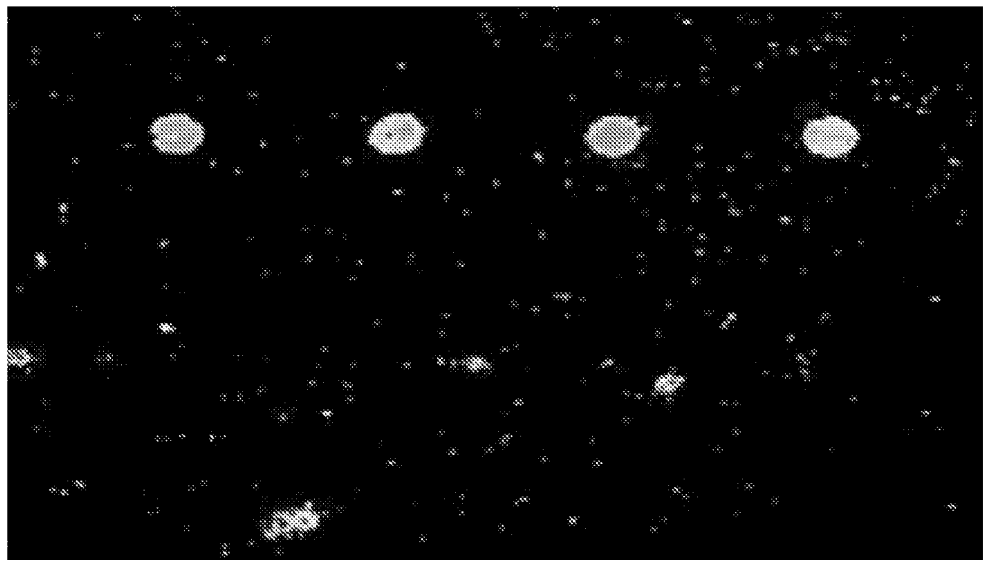
FIG. 11 shows the fluorescence image obtained after PCR of genomic DNA on the dendron surface with the use of a capture probe as a PCR primer. The DNA was denatured at 87° C. during PCR cycles.

FIG. 11 shows the fluorescence image obtained after PCR on the dendron surface. Only the capture probe attached to the dendron (forward primer) and the soluble reverse primer participated in the amplification of the desired DNA sequence from genomic DNA. Note that only the wild type sequence on the chip slide was fluorescently labeled since HEK293 cells have the wild type codon 248 of p53 gene in the genome.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for detecting a nucleic acid molecule in a sample, said method comprising i) amplifying a nucleic acid molecule, in a sample, by use of two primers in a polymerase chain reaction (PCR) in the presence of a single stranded nucleic acid probe that is complementary to said nucleic acid molecule, wherein an end of said probe is immobilized via attachment to the apex of a conical dendron that is attached to a solid surface by the base of said conical dendron, ii) completing the last cycle of the PCR to produce amplified nucleic acid molecule, iii) denaturing said amplified nucleic acid material in the presence of said PCR reaction mixture to form a denatured mixture in the presence of the immobilized probe and attached conical dendron, iv) allowing said amplified nucleic acid material, after denaturation, within the same PCR reaction mixture, to hybridize to said probe to form a double stranded complex in the presence of said denatured mixture, and v) detecting said double stranded complex attached to said solid surface.

2. The method according to claim 1, wherein said probe comprises a sequence used as one of the primers in said polymerase chain reaction.

3. The method of claim 1 wherein said solid surface is in contact with a thermocycler capable of regulating the temperature, temperature cycle times, and number of temperature cycles in said solid surface.

4. The method of claim 3 wherein said regulating is automatically controlled by said thermocycler.

5. The method of claim 1 wherein said sample comprises whole blood, one or more cells, or a virus or viral particle.

6. The method of claim 2 wherein said sample comprises whole blood, one or more cells, or a virus or viral particle; or said nucleic acid molecule is in a cell-free sample; or said nucleic acid molecule is in a viral particle, or in a non-eukaryotic cell, in said sample; or said nucleic acid molecule is a DNA molecule, optionally a genomic DNA molecule; or said nucleic acid molecule is of a pathogen; or said nucleic acid molecule comprises a mutated sequence and said probe is complementary to said mutated sequence; or said nucleic acid molecule is a cDNA molecule prepared by reverse transcription of an RNA molecule, such as a viral RNA molecule, in said sample, wherein said RNA molecule is optionally from a eukaryotic cell, a non-eukaryotic cell, or a virus or viral particle.

7. The method of claim 1 wherein
said detecting comprises contacting said complex with a detectable label which binds double stranded DNA to form a detectably labeled complex, and detecting the labeled complex.

8. The method of claim 2 wherein
said detecting comprises contacting said complex with a detectable label which binds double stranded DNA to form a detectably labeled complex, and detecting the labeled complex.

9. The method of claim 1 wherein said nucleic acid molecule is in a cell-free sample.

10. The method of claim 1 wherein said nucleic acid molecule is in a viral particle, or in a non-eukaryotic cell, in said sample.

11. The method of claim 1 wherein said nucleic acid molecule is a DNA molecule.

12. The method of claim 11 wherein said DNA molecule is a genomic DNA molecule.

13. The method of claim 1 wherein said nucleic acid molecule is of a pathogen.

14. The method of claim 1 wherein said nucleic acid molecule comprises a mutated sequence and said probe is complementary to said sequence.

15. The method of claim 1 wherein said nucleic acid molecule is a cDNA molecule prepared by reverse transcription of an RNA molecule in said sample.

16. The method of claim 15 wherein said RNA molecule is a viral RNA molecule.

17. The method of claim 15 wherein said RNA molecule is from a eukaryotic cell, a non-eukaryotic cell, or a virus or viral particle.

18. The method of claim 1 wherein said amplifying comprises use of a primer, or nucleotide triphosphate, which is attached to a detectable label and incorporated into said amplified nucleic acid material, and wherein said detecting comprises a detection of said label.

19. The method of claim 18 wherein said detectable label is a fluorescent label.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Forward primer

<400> SEQUENCE: 1
tactcccctg ccctcaacaa                                              20

<210> SEQ ID NO 2
<211> LENGTH: 23
<212> TYPE: DNA
<213> ORGANISM: Artificial Sequence
<220> FEATURE:
<223> OTHER INFORMATION: Reverse primer

<400> SEQUENCE: 2
ctggagtctt ccagtgtgat gat                                          23

<210> SEQ ID NO 3
<211> LENGTH: 21
<212> TYPE: DNA
<213> ORGANISM: Artificial Sequence
<220> FEATURE:
<223> OTHER INFORMATION: Capture probe oligonucleotide
<220> FEATURE:
<221> NAME/KEY: misc_feature
<222> LOCATION: (11)..(11)
<223> OTHER INFORMATION: g, a, t, or c

<400> SEQUENCE: 3
```
tcgacatagt ntggtggtgc c       21

<210> SEQ ID NO 4
<211> LENGTH: 19
<212> TYPE: DNA
<213> ORGANISM: Artificial Sequence
<220> FEATURE:
<223> OTHER INFORMATION: Capture probe for detection of codon 1896-wild
      type

<400> SEQUENCE: 4
ggtttggggc atggacatt       19

<210> SEQ ID NO 5
<211> LENGTH: 19
<212> TYPE: DNA
<213> ORGANISM: Artificial Sequence
<220> FEATURE:
<223> OTHER INFORMATION: Capture probe for detection of codon
      1896-mutant type

<400> SEQUENCE: 5
ggtttagggc atggacatt       19

<210> SEQ ID NO 6
<211> LENGTH: 20
<212> TYPE: DNA
<213> ORGANISM: Artificial Sequence
<220> FEATURE:
<223> OTHER INFORMATION: Forward primer

<400> SEQUENCE: 6
ttaaggactg ggaggagctg       20

<210> SEQ ID NO 7
<211> LENGTH: 24
<212> TYPE: DNA
<213> ORGANISM: Artificial Sequence
<220> FEATURE:
<223> OTHER INFORMATION: Reverse primer

<400> SEQUENCE: 7
gctccaaatt ctttataagg gtca       24

<210> SEQ ID NO 8
<211> LENGTH: 18
<212> TYPE: DNA
<213> ORGANISM: Artificial Sequence
<220> FEATURE:
<223> OTHER INFORMATION: Capture probe for codon 175 in p53 gene
<220> FEATURE:
<221> NAME/KEY: misc_feature
<222> LOCATION: (11)..(11)
<223> OTHER INFORMATION: g, a, t, or c

<400> SEQUENCE: 8
gttgtgaggc nctgcccc       18

<210> SEQ ID NO 9
<211> LENGTH: 21
<212> TYPE: DNA
<213> ORGANISM: Artificial Sequence
<220> FEATURE:
<223> OTHER INFORMATION: Capture probe for codon 215 in the p53 gene
<220> FEATURE:
<221> NAME/KEY: misc_feature
<222> LOCATION: (11)..(11)
<223> OTHER INFORMATION: g, a, t, or c

```
<400> SEQUENCE: 9
tttcgacata ntgtggtggt g                                              21

<210> SEQ ID NO 10
<211> LENGTH: 23
<212> TYPE: DNA
<213> ORGANISM: Artificial Sequence
<220> FEATURE:
<223> OTHER INFORMATION: Forward primer

<400> SEQUENCE: 10
ttcaactctg tctccttcct ctt                                            23

<210> SEQ ID NO 11
<211> LENGTH: 24
<212> TYPE: DNA
<213> ORGANISM: Artificial Sequence
<220> FEATURE:
<223> OTHER INFORMATION: Reverse primer

<400> SEQUENCE: 11
gttataggga ggtcaaataa gcag                                           24

<210> SEQ ID NO 12
<211> LENGTH: 21
<212> TYPE: DNA
<213> ORGANISM: Artificial Sequence
<220> FEATURE:
<223> OTHER INFORMATION: Capture probe for codon 248 in the p53 gene
<220> FEATURE:
<221> NAME/KEY: misc_feature
<222> LOCATION: (21)..(21)
<223> OTHER INFORMATION: g, a, t, or c

<400> SEQUENCE: 12
gaaacacttt tcgacatagt n                                              21
```